(12) United States Patent
Ishimito et al.

(10) Patent No.: US 6,506,167 B1
(45) Date of Patent: Jan. 14, 2003

(54) BLOOD-COLLECTING TUBES

(75) Inventors: Tetsushi Ishimito, Matsubara (JP); Yasuyuki Nakamura, Moriguchi (JP); Katsutoshi Hamada, Osaka (JP)

(73) Assignee: I-Design Co., Ltd., Osaka (JP)

( * ) Notice: Subject to any disclaimer, the term of this patent is extended or adjusted under 35 U.S.C. 154(b) by 84 days.

(21) Appl. No.: 09/641,585

(22) Filed: Aug. 18, 2000

Related U.S. Application Data

(63) Continuation of application No. 09/219,905, filed on Dec. 23, 1998, now abandoned.

(30) Foreign Application Priority Data

Dec. 24, 1997 (JP) .............................................. 9-354859

(51) Int. Cl.[7] .............................. A61B 5/00; B65D 81/00
(52) U.S. Cl. ..................................................... 600/577
(58) Field of Search ................................ 600/577, 573, 600/576, 583; 210/645, 504, 505, 767; 436/177

(56) References Cited

U.S. PATENT DOCUMENTS

| | | | |
|---|---|---|---|
| 3,920,557 A | 11/1975 | Ayres | 210/516 |
| 4,960,130 A | 10/1990 | Guirguis | 128/760 |
| 5,364,533 A | * 11/1994 | Ogura et al. | 210/645 |
| 5,471,994 A | 12/1995 | Guirguis | 128/760 |
| 5,683,355 A | 11/1997 | Fini et al. | 604/4 |
| 5,766,314 A | 6/1998 | Weber et al. | 95/220 |

* cited by examiner

*Primary Examiner*—Kevin Shaver
*Assistant Examiner*—Brian Szmal
(74) *Attorney, Agent, or Firm*—Rosenthal & Osha L.L.P.

(57) ABSTRACT

An object of the invention is to achieve an increased speed of blood collection and separation as well as ease of handling of plasma components after blood separation. A blood-collecting tube, which draws in blood and separates it by using an internal negative pressure in the tube, comprises an upstream tube 10 having a blood inlet 11 and blood outlets 18, a filter 20 for separating blood and a downstream tube 12. A plug 18 is fitted to the blood inlet 11 to thereby close the interior of the upstream tube 10, and the filter 20 is installed so that it blocks the blood outlets 18. The downstream tube 12 is disposed to enclose the filter 20 and constructed in such a way that the downstream tube 12 can be attached to and detached from the upstream tube 10.

9 Claims, 14 Drawing Sheets

BLOOD-COLLECTING TUBES

CROSS-REFERENCE TO RELATED APPLICATIONS

This application is a continuation of U.S. patent application Ser. No. 09/219,905, filed Dec. 23, 1998 abandoned.

BACKGROUND OF THE INVENTION

This invention is concerned with blood-collecting tubes capable of collecting blood and separating it at the same time.

Conventionally, blood collection and separation have involved the processes of withdrawing blood by means of a syringe, for instance, injecting the collected blood into test tubes, mounting the test tubes in a centrifugal separator, and operating the centrifugal separator to separate the blood into its cellular and plasma components by using a difference in their relative densities. This method has one drawback, however, in that it requires a great deal of time and labor from the start of blood collection up to the end of blood separation, because blood collection and separation must be carried out by using completely different facilities.

Under this circumstance, there has been a move in recent years to develop blood-collecting tubes which make it possible to separate blood immediately where it was collected. As an example, Japanese Official Gazette No. 2526889 for utility model applications discloses a blood-collecting tube which is constructed such that a partition plate is provided in a main tubular body, dividing it into an upstream compartment and a downstream compartment, both ends of U-shaped, porous hollow-fiber membranes are attached to the partition plate, their both ends opening to the upstream compartment, and a vacuum is created in the internal space of the main tubular body. When blood is sucked into the upstream compartment of this tube through a blood-drawing needle, the pressure in the upstream compartment increases by an amount corresponding to the amount of the blood drawn into the upstream compartment, and this causes a pressure difference between the upstream and downstream compartments. Due to this pressure difference, the blood enters the lumen of each hollow-fiber membrane through its openings at both ends. Since the hollow-fiber membranes allow only the plasma components of the blood to pass through, the blood is separated into the cellular components in the upstream compartment and the plasma components in the downstream compartment on both sides of the partition plate.

This blood-collecting tube, however, is associated with problems to be solved as cited below:

1) The manufacture of this blood-collecting tube involves the need to perform such work as fixing a large number of U-shaped hollow-fiber membranes to the partition plate and fixing the partition plate at a specified position within the main tubular body. This requires a great deal of effort and makes it impossible to avoid high costs.

2) To examine the plasma components which have flown into the downstream compartment, it is necessary to first suck the plasma components out of the downstream compartment by using another instrument (e.g., a syringe) and then inject the plasma components into a separate vessel (e.g., a test tube). Therefore, there is such inconvenience that even when the plasma components have been successfully separated, subsequent collection of the plasma components could require much time.

3) Although a large number of hollow-fiber membranes are used, they provide a limited surface area since each hollow-fiber membrane has a filament-shaped structure and, thus, blood separation takes substantial time. Furthermore, the hollow-fiber membranes are apt to cause clogging within themselves.

SUMMARY OF THE INVENTION

An object of this present invention is to solve the aforementioned problems.

In order to fulfil the above object according to this invention, a blood-collecting tube comprising: an upstream tube having a blood inlet and a blood outlet; a plug fitted to the blood inlet of the upstream tube for closing the upstream tube, the plug adapted for being pierced by a blood-drawing needle; a filter for covering the whole area of the blood outlet of the upstream tube and for separating blood into cellular and plasma components; and a downstream tube for enclosing the filter and the blood outlet and the interior of the downstream tube is sealed, and the downstream tube is attachable to and detachable from the upstream tube.

According to the blood-collecting tube, it is possible to carry out blood collection and separation in an efficient manner by the following procedure:

(1) The interior of both the upstream tube and the downstream tube is depressurized by piercing the plug with a suction tube, for instance. This depressurizing operation may be performed immediately before shipment. More specifically, each blood-collecting tube may be delivered after it has been depressurized by a manufacturer.

(2) After sticking one end of the blood-drawing needle into a blood vessel, its other end is passed through the plug. At this point, blood automatically flows into the upstream tube due to a negative pressure within the upstream tube, and a pressure difference corresponding to the amount of the blood drawn in is produced between the upstream tube and the downstream tube. Due to this pressure difference, the blood gains a tendency to flow into the downstream tube through the blood outlet. However, because the filter is disposed at the blood outlet and only the plasma components are allowed to pass through the filter, the plasma components are separated from the cellular components and flow into the downstream tube. Thus, separation of the blood is performed at the same time as it is being collected. This invention, however, is not necessarily limited to blood-collecting tubes designed to separate the blood into its cellular and plasma components in an extremely strict fashion but includes those which allow quite a limited portion of the cellular components having relatively small diameters (e.g., platelets) to pass through the filter.

(3) Upon completion of blood collection, the downstream tube is removed from the upstream tube. Since only the plasma components have been collected in this downstream tube, the downstream tube can be used as it is as a test tube in subsequent examination.

Other objects, features and advantages of the present invention will become readily apparent from reading of the following description which has been prepared in conjunction with the accompanying drawings.

DETAILED DESCRIPTION OF THE PREFERRED EMBODIMENTS OF THE INVENTION

Figure 1:
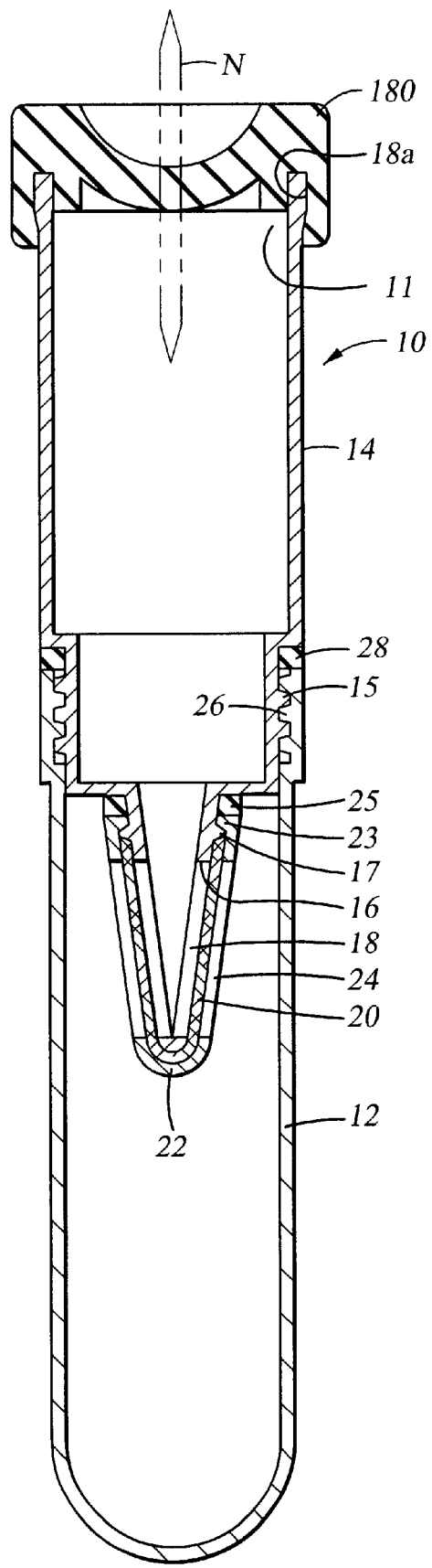
FIG. 1 is a cross-sectional front view of a blood-collecting tube according to a first embodiment of the present invention.

A first embodiment of this invention is described with reference to FIGS. 1 and 2.

A blood-collecting tube illustrated comprises an upstream tube 10 and a downstream tube 12.

An upper end of the upstream tube 10 forms an opening which serves as a blood inlet 11. A plug 180 made of an elastic material, such as rubber, is fitted into the blood inlet 11 to close it off. More specifically, a circular groove 18a is formed in a bottom surface of the plug 180 and a peripheral portion of the blood inlet 11 (or an upper end portion of the upstream tube 10) is pressed into the circular groove 18a to thereby fit the plug 180 to the upstream tube 10.

At a lower portion of the upstream tube 10, an externally threaded part 15 which is more slender than a main cylindrical body 14 of the upstream tube 10 and a filter-mounting part 16 having a generally triangular shape are formed in this order downward, with external threads formed around a curved outer surface of the externally threaded part 15. While a lower end of the filter-mounting part 16 is closed off, there are formed blood outlets 18 connecting the inside and outside of the filter-mounting part 16 in both left and right side surfaces (inclined surfaces) of the filter-mounting part 16 immediately above its lower end.

A rectangular filter 20, which covers almost the whole area of the filter-mounting part 16 including the blood outlets 18, is fitted outside the blood outlets 18. This filter 20 would be good enough if it has the ability to roughly separate blood into its cellular and plasma components. The filter 20 may be of a type which allows the passage of quite a limited portion of the cellular components (e.g., cellular components having relatively small diameters, such as platelets).

To give some specific examples, a commonly available membrane filter may be used for capturing blood cells by utilizing its molecular-sieve function, or glass fibers may be employed to adsorb the blood cells. It is also possible to capture the cellular components with ordinary filter paper having large-diameter pores, if it is impregnated with anti-hemocyte antibody to thereby utilize specific binding action between the antibody and blood cells. Furthermore, it is possible to separate blood at higher efficiency if the filter is impregnated with cationic macromolecular substance so that the cellular components (especially red blood cells), whose surfaces are negatively charged, would become aggregated forming large masses by their electrostatic force.

It is also possible to reliably prevent filter clogging by cellular components and separate blood at higher efficiency by using a filter constructed of more than one type of porous material which is laminated in such a way that pore diameters become progressively smaller from upstream side to downstream side (from top to bottom in the illustrated example). This kind of laminated structure may be produced by simply stacking a plurality of porous layers having different pore diameters or by previously laminating such layers into a single structure. A filter formed by laminating three layers of porous membranes individually having average pore diameters of 0.5 to 3.0 micrometers, 3.0 to 8.0 micrometers, and 8.0 to 30 micrometers was used in practice, form which it has been ascertained that the filter demonstrated its ability to properly separate blood without causing any clogging problem.

This filter is applicable also to a later-described second embodiment and other succeeding embodiments.

On the outside of the filter 20, there is fitted a filter retainer 22. The filter retainer 22 has a generally V-shaped structure which makes it possible to sandwich the filter 20 between the filter-mounting part 16 and the filter retainer 22, and passages 24 which match the blood outlets 18 are formed in both side walls of the filter retainer 22. There are formed snap-on protrusions 23 projecting inward at an upper end of the filter-mounting part 16. On the other hand, snap-on protrusions 17 projecting outward are formed at an upper end portion of the filter-mounting part 16. The filter retainer 22 is fixed onto the filter-mounting part 16 with the filter 20 held between the filter retainer 22 and the filter-mounting part 16 when the snap-on protrusions 17 are forced over the snap-on protrusions 23 until they are engaged with each other. Further, a ring-shaped sealing element 25 is fitted between the upper end of the filter retainer 22 and a lower end surface of the externally threaded part 15.

The specific structure for fixing the filter retainer 22 to the filter-mounting part 16 is not limited to that of the illustrated example. It would also be possible to eliminate the filter retainer 22 and fix the filter 20 to inner side surfaces of the filter-mounting part 16. The aforementioned structure employing the filter retainer 22, however, provides an advantage that it makes it easier to mount the filter 20.

The downstream tube 12 has an opening at its upper end only, with internal threads 26 formed in an inner surface of the downstream tube 12 close to its open end. When the internal threads 26 mate with the aforementioned external threads of the externally threaded part 15, the two tubes 10, 12 are directly joined, whereby the filter 20 and the filter-mounting part 16 are completely enclosed by the downstream tube 12.

Although the internal space of the downstream tube 12 can be closed off only by mating the aforementioned threads, a sealing element 28 is placed between the upper end of the downstream tube 12 and a lower end surface of the main body 14 of the upstream tube 10 as well to provide more reliable sealing.

The structure for joining the upstream tube 10 and the downstream tube 12 is not limited to the aforementioned one which is achieved by mating the threads. One alternative arrangement, for example, is such that a ring-shaped rubber layer is provided on a curved inner surface of the downstream tube 12 close to its upper open end and the lower portion of the upstream tube 10 is pushed into the inside of the rubber layer. The earlier-mentioned joining method employing the threads which can mate with each other, however, provides an advantage that the two tubes 10, 12 can be detachably joined with a simple structure, yet achieving high sealing performance.

The operating procedure and features of the blood-collecting tube according to the present embodiment are described below.

First, with the upstream tube 10 and the downstream tube 12 joined directly together, the plug 180 is pierced with a suction tube so that its one end is positioned within the internal space of the upstream tube 10. Then, air within the upstream tube 10 and the downstream tube 12 is sucked to thereby depressurize the interior of the two tubes 10, 12. The degree of vacuum to be achieved by this operation may be properly determined according to the specifications of the blood-collecting tube. This depressurizing operation may be performed by a manufacturer immediately before shipment so that each blood-collecting tube is delivered in a readily depressurized condition.

Figure 2A:
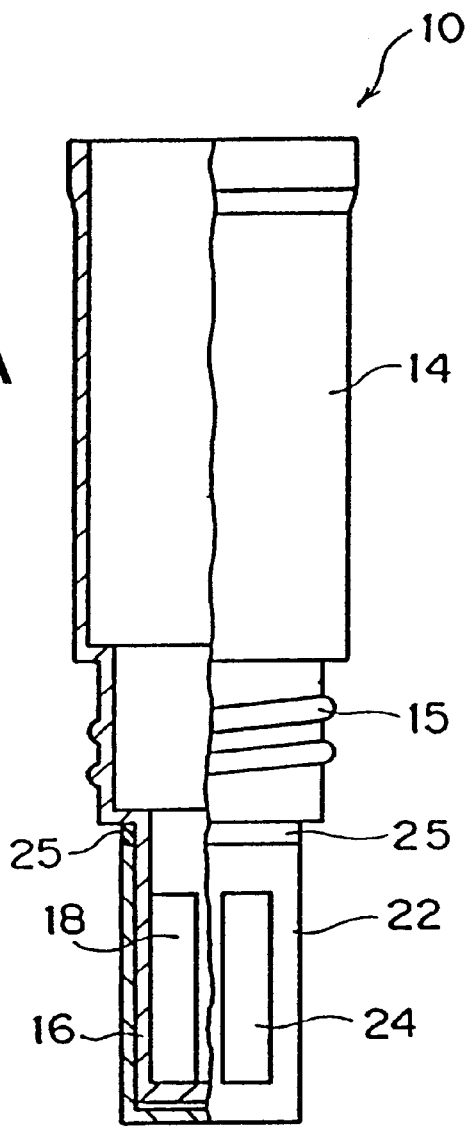
FIG. 2A is a partially sectional front view of an upstream tube constituting part of the blood-collecting tube of FIG. 1.
Figure 2B:
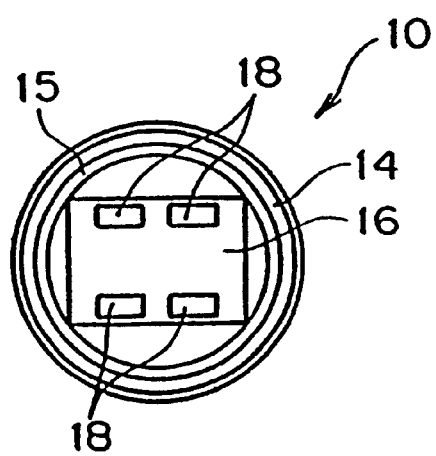
FIG. 2B is its bottom view.

Next, one end (upper end as illustrated) of a blood-drawing needle N as shown by alternate long and two short dashed lines in FIG. 1 is stuck into a blood vessel of a subject to be examined and the other end (lower end in FIG. 1) is passed through the plug 180 so that the plug 180 is pierced by the blood-drawing needle N. Consequently, blood in the blood vessel automatically flows into the upstream tube 10 due to a negative pressure within the upstream tube 10. Then, as the pressure within the upstream tube 10 becomes higher than the pressure within the downstream tube 12 by an amount corresponding to the amount of the blood drawn in, the blood gains a tendency to flow into the downstream tube 12 through the blood outlets 18 due to a resultant pressure difference.

However, because the filter 20 is disposed at the blood outlets 18 as if to block blood flow, passage of cellular components contained in the blood is prohibited while only its plasma components are allowed to pass through the filter 20 into the downstream tube 12. Thus, separation of the blood is performed at the same time as it is being collected. Furthermore, because the filter 20 through which the blood passes has a larger area than a conventional filter employing hollow-fiber membranes, for example, it is possible to perform blood separation at an increased rate.

After the plasma components have been collected into the downstream tube 12 in this manner, the downstream tube 12 may be separated from the upstream tube 10 by relatively turning the upstream tube 10 and the downstream tube 12 to unscrew the externally threaded part 15 and the internal threads 26. Since only the plasma components are accumulated in the downstream tube 12, it is possible to use the downstream tube 12 as it is as a test tube in subsequent examination.

Figure 3:
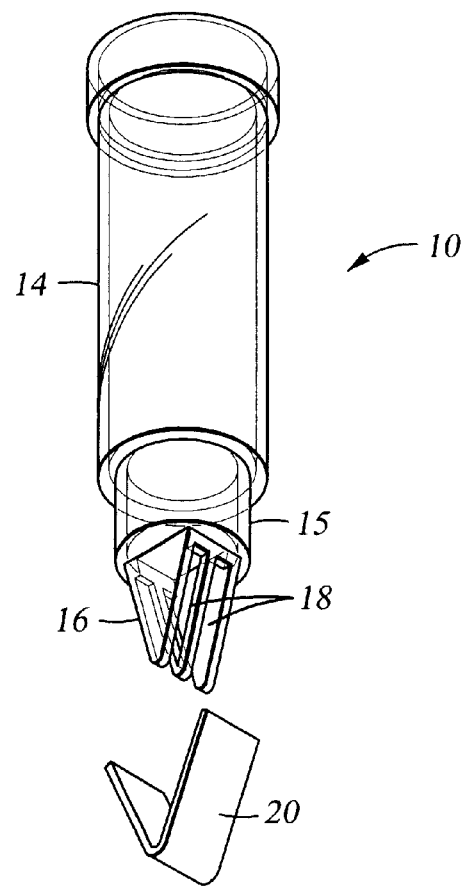
FIG. 3 is an exploded perspective view of a blood-collecting tube according to a second embodiment of the invention.
Figure 3:
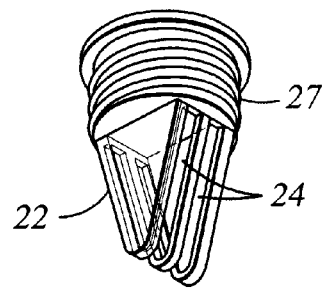
Figure 3:
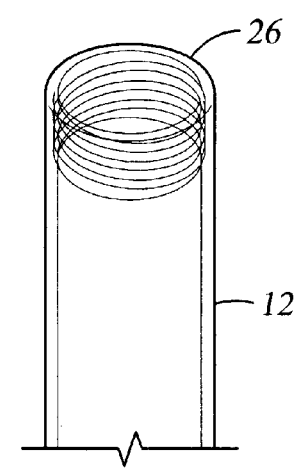

A second embodiment of the invention is depicted in FIG. 3, in which a simple cylindrical part 15' is formed in place of the externally threaded part 15 of the upstream tube 10 depicted in FIG. 1 and the shape of a filter retainer 22 is determined so as to cover a lower portion of an upstream tube 10 including the cylindrical part 15'. Further, external threads 27 are formed in a curved outer surface of the filter retainer 22, and the upstream tube 10 and a downstream tube 12 are joined with each other by screwing the external threads 27 into internal threads 26 of the downstream tube 12.

As described above, it is not absolutely necessary to form threads directly in the upstream tube 10, but the upstream tube 10 and the downstream tube 12 can be joined together by forming threads in the filter retainer 22 which is an element disposed on the same side as the upstream tube 10.

Figure 4:
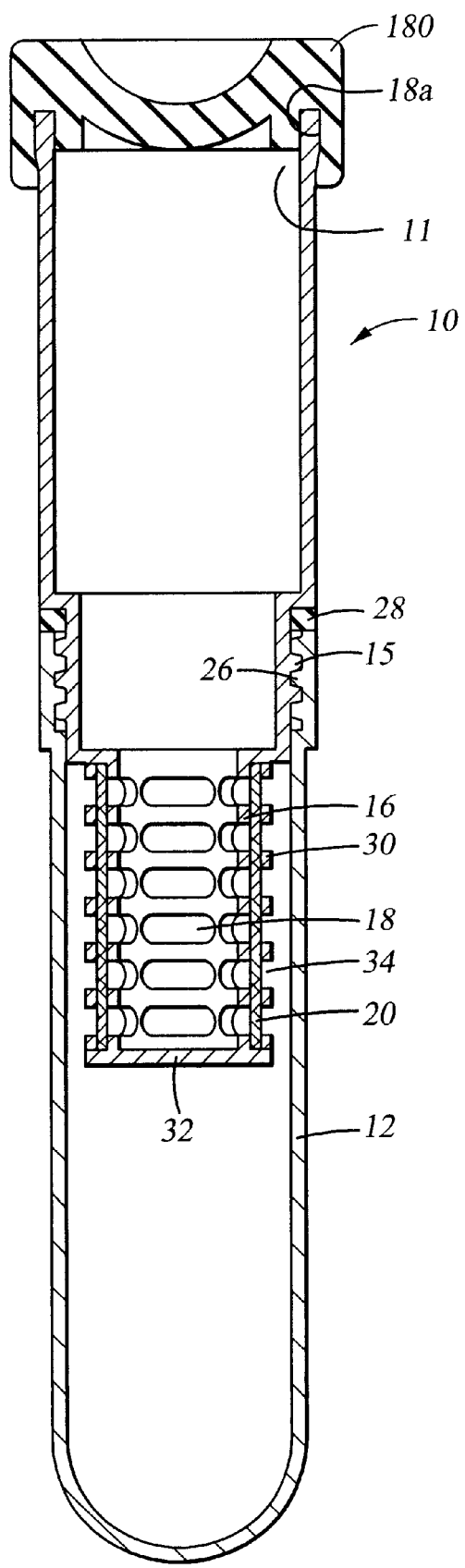
FIG. 4 is a cross-sectional front view of a blood-collecting tube according to a third embodiment of the invention.
Figure 5A:
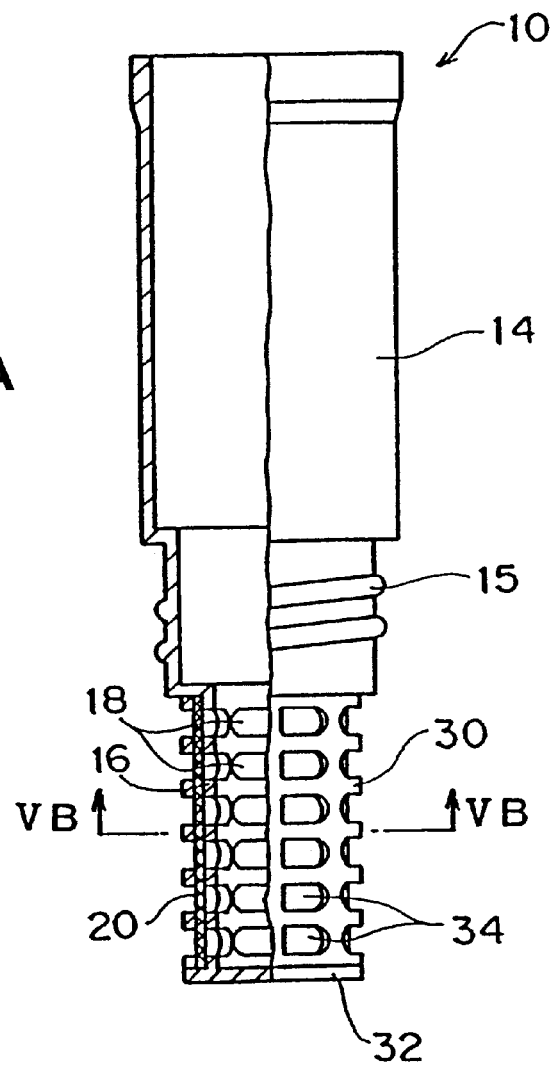
FIG. 5A is a partially sectional front view of an upstream tube constituting part of the blood-collecting tube of FIG. 4.

A third embodiment of the invention is depicted in FIGS. 4 and 5. In this embodiment, a filter-mounting part 16 is formed into a cylindrical structure having a bottom plate 32 and a number of blood outlets 18 are formed in a cylindrical surrounding wall of the filter-mounting part 16. A filter 20 having a generally rectangular shape is used in this embodiment as well, the filter 20 being wound around the filter-mounting part 16 in cylindrical form. Further, a filter retainer 30 is fitted on the outside of the filter 20 and fixed to the filter-mounting part 16 to thereby hold the filter 20 in position.

Figure 5B:
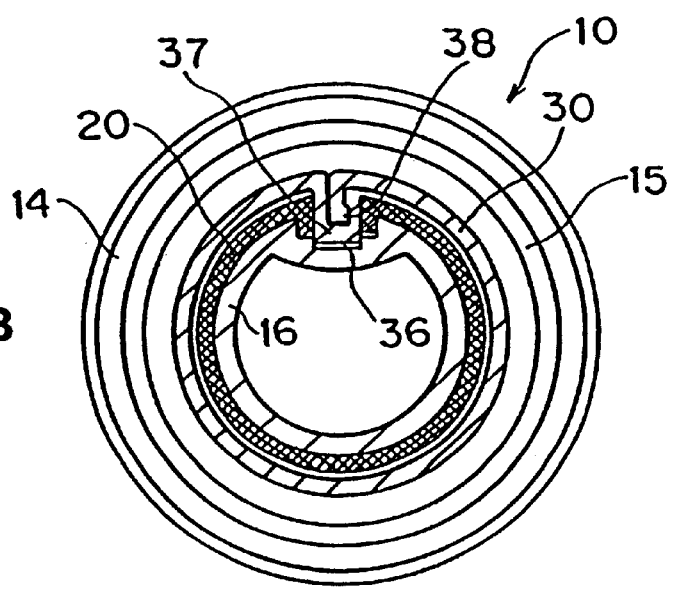
FIG. 5B is a cross-sectional view taken along lines VB—VB of FIG. 5A.

The filter retainer 30 of this embodiment is produced in sheet form using such a material as a synthetic resin which can deflect. The filter retainer 30 is shaped such that it can be wound around the filter 20 and has a number of passages 34 which match the aforementioned blood outlets 18 when the filter retainer 30 is wound around the filter 20. As shown in FIG. 5B, a recess 36 is formed at an appropriate position in a curved outer surface of the filter-mounting part 16. On the other hand, joining parts 37 and 38 which mate with each other are formed at both ends of the filter retainer 30. With these joining parts 37, 38 snapped on each other, they are fitted into the aforementioned recess 36, whereby the filter retainer 30 is secured on the filter-mounting part 16 with the filter 20 sandwiched between the filter-mounting part 16 and the filter retainer 30.

According to this construction, it is possible to achieve such advantage that the area of the filter 20 through which blood passes can be further increased by increasing the axial length of the cylinder-shaped filter-mounting part 16.

Figure 6:
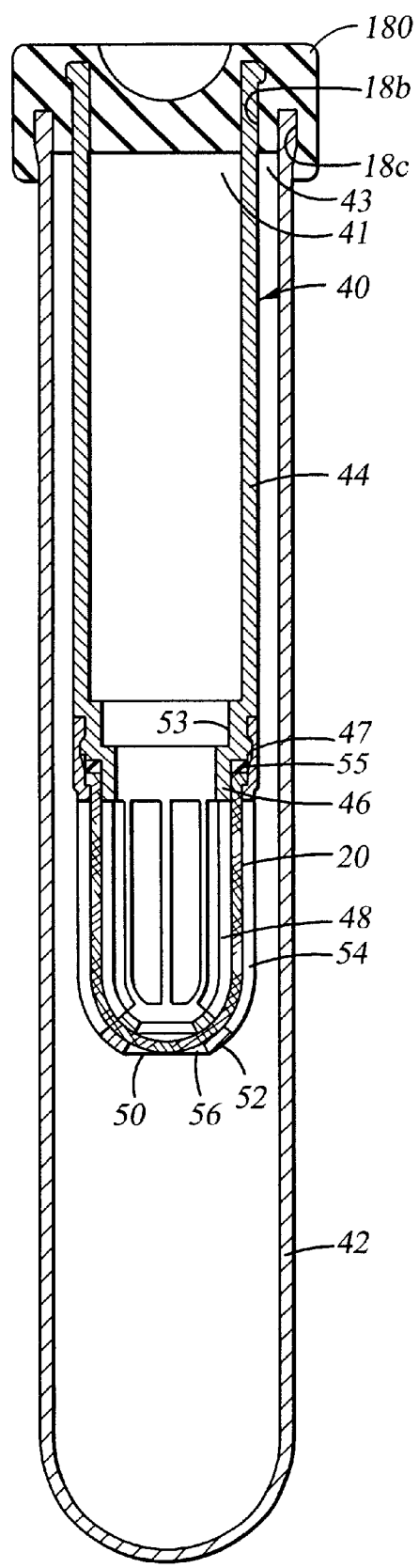
FIG. 6 is a cross-sectional front view of a blood-collecting tube according to a fourth embodiment of the invention.
Figure 7A:
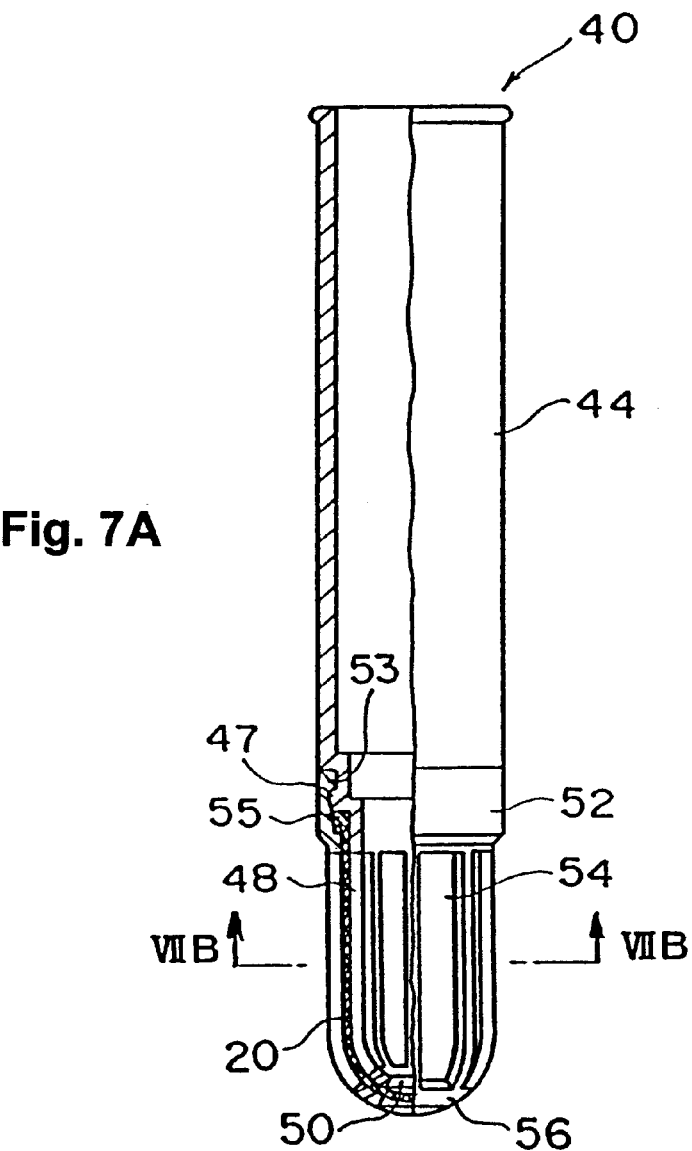
FIG. 7A is a partially sectional front view of an upstream tube constituting part of the blood-collecting tube of FIG. 6.
Figure 7B:
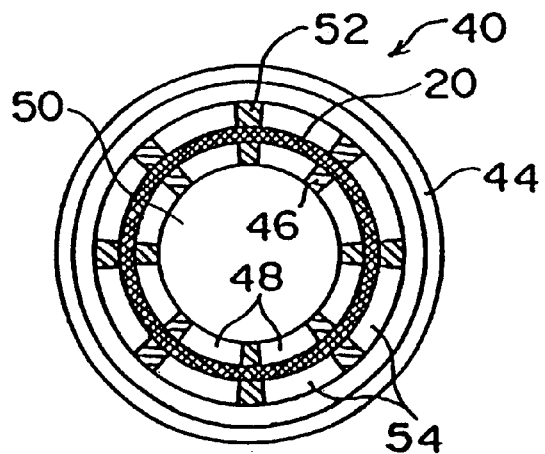
FIG. 7B is a cross-sectional view taken along lines VIIB—VIIB of FIG. 7A.

A fourth embodiment of the invention is depicted in FIGS. 6 and 7.

This embodiment employs an internal-external double-tube structure in which the whole of an upstream tube 40 is completely accommodated within a downstream tube 42. The upstream tube 40 has at its upper end a blood inlet 41 forming an opening and, at its lower portion, a filter-mounting part 46 which is more slender than a main cylindrical body 44 of the upstream tube 40. The filter-mounting part 46 has a generally hemispherical bottom portion. Blood outlets 50 and 48 are provided in the bottom portion and a side portion of the filter-mounting part 46, respectively.

A filter 20 is disposed to cover almost the whole area (at least a region including the blood outlets 50, 48) of the aforementioned filter-mounting part 46 and a filter retainer 52 is fitted on the outside of the filter 20, whereby the filter 20 is sandwiched between the filter-mounting part 46 and the filter retainer 52.

This filter retainer 52 forms a caplike structure to cover the whole of the filter-mounting part 46 from its bottom side and has passages 54, 56 which match the aforementioned blood outlets 50, 48 when the filter retainer 52 is fitted to the filter-mounting part 46. A snap-on protrusion 53 projecting inward is formed at an upper end of the filter retainer 52 while a snap-on protrusion 47 projecting outward is formed at an upper end of the filter-mounting part 46. In this structure, the filter retainer 52 is fixed to the upstream tube 40 when the snap-on protrusion 53 is forced over the snap-on protrusion 47 (that is, when both protrusions 47, 53 mate with each other). Further, a ring-shaped sealing element 55, which is placed between the filter-mounting part 46 and the filter retainer 52, is positioned immediately above the filter 20.

The downstream tube 42, which is larger than the upstream tube 40, is of a shape having an opening 43 at an upper end only, and a peripheral portion of the opening 43, together with a peripheral portion of the blood inlet 41 of the upstream tube 40, is fitted into a common plug 180. Specifically, inner and outer circular grooves 18b, 18c are formed in a bottom surface of the plug 180, and both tubes 40, 42 are detachably fitted to the plug 180 by pushing the peripheral portions of the blood inlet 41 and the opening 43 into the respective grooves 18b, 18c.

It is possible to introduce blood into the upstream tube 40 by sticking one end of a blood-drawing needle N as shown in FIG. 1 into a blood vessel with both of the tubes 40, 42 readily fitted to the plug 180 and the interior of the tubes 40, 42 held in a depressurized condition, and passing the other end of the blood-drawing needle N through a central part of the plug 180 in this blood-collecting tube as well. Then, it is possible to cause only plasma components to flow into the outer downstream tube 42 through the filter 20 due to a pressure increase within the upstream tube 40. This means that the blood can be separated. Upon completion of blood separation, only the downstream tube 42 is removed (that is, the downstream tube 42 is separated from the upstream tube 40) so that the downstream tube 42 can be used as it is as a test tube for the plasma components in subsequent examination.

Figure 8:
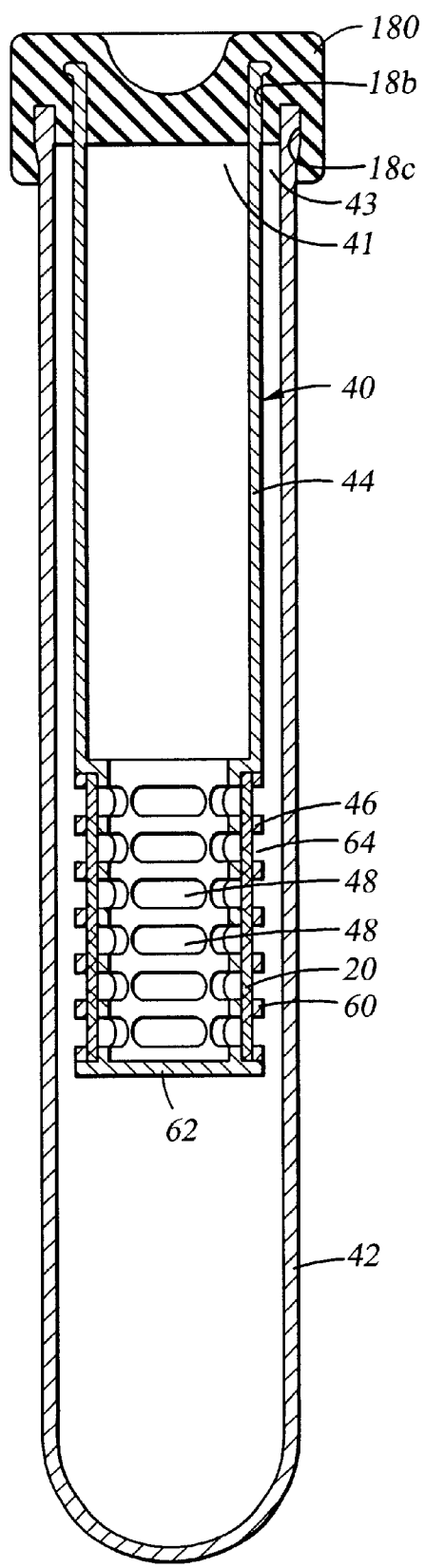
FIG. 8 is a cross-sectional front view of a blood-collecting tube according to a fifth embodiment of the invention.
Figure 9A:
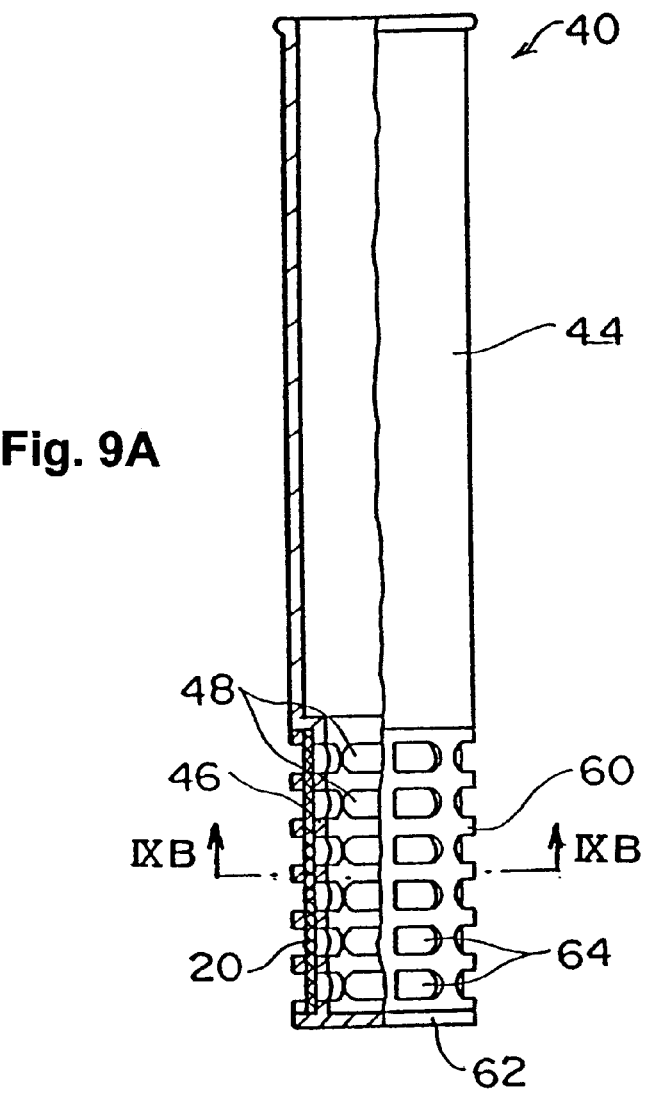
FIG. 9A is a partially sectional front view of an upstream tube constituting part of the blood-collecting tube of FIG. 8.

A fifth embodiment of the invention is depicted in FIGS. 8 and 9.

Figure 9B:
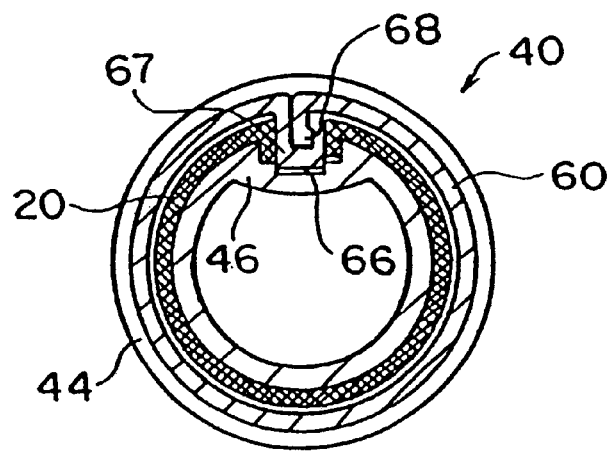
FIG. 9B is a cross-sectional view taken along lines IXB—IXB of FIG. 9A.

In this embodiment, the lower portion of the upstream tube 40 shown in the foregoing fourth embodiment is made completely identical to the structure of the lower portion of the upstream tube 10 shown in the earlier-described third embodiment. Specifically, a filter-mounting part 46 is formed into a cylindrical structure having a bottom plate 62 with a number of blood outlets 48 formed in a cylindrical surrounding wall of the filter-mounting part 46, a filter 20 having a generally rectangular shape is wound around the filter-mounting part 46 in cylindrical form, and the filter 20 is sandwiched between a filter retainer 60 fitted on the outside of the filter 20 and the filter-mounting part 46. This filter retainer 60 is produced in sheet form using such a material as a synthetic resin which can deflect and is shaped such that it can be wound around the filter 20. The filter retainer 60 has a number of passages 64 which match the aforementioned blood outlets 48 when the filter retainer 60 is wound around the filter 20. Joining parts 67 and 68 formed at both ends of the filter retainer 60 and engaged with each other are fitted into a recess 66 which is formed at an appropriate position in a curved outer surface of the filter-mounting part 46 as shown in FIG. 9B, whereby they are held in a securely engaged condition and the filter retainer 60 is fixed to the filter-mounting part 46 with the filter 20 sandwiched between the filter-mounting part 46 and the filter retainer 60.

It is possible to further increase the area of the filter 20 through which blood passes by increasing the axial length of the cylinder-shaped filter-mounting part 46 in this construction as well, as in the construction of the earlier-described third embodiment.

Figure 10:
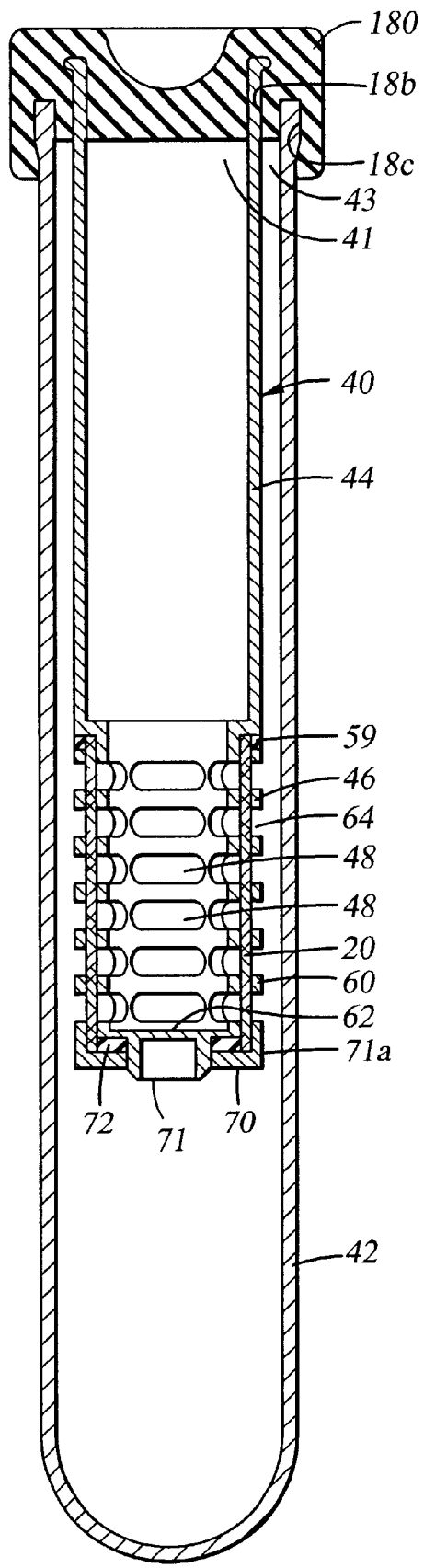
FIG. 10 is a cross-sectional front view of a blood-collecting tube according to a sixth embodiment of the invention.
Figure 11A:
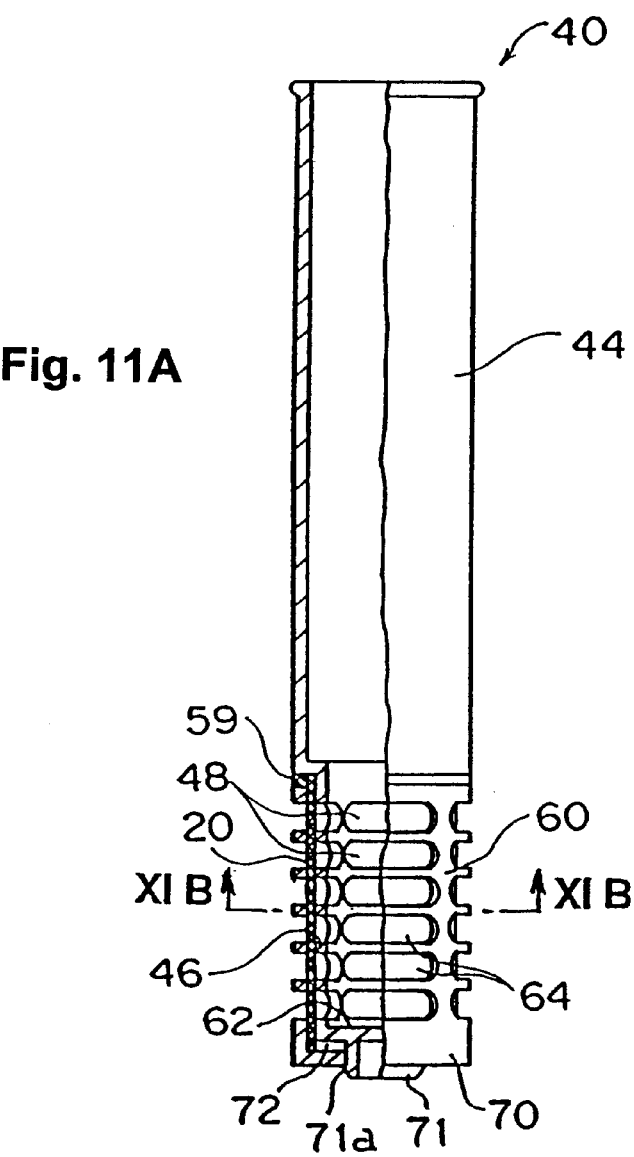
FIG. 11A is a partially sectional front view of an upstream tube constituting part of the blood-collecting tube of FIG. 10.
Figure 11B:
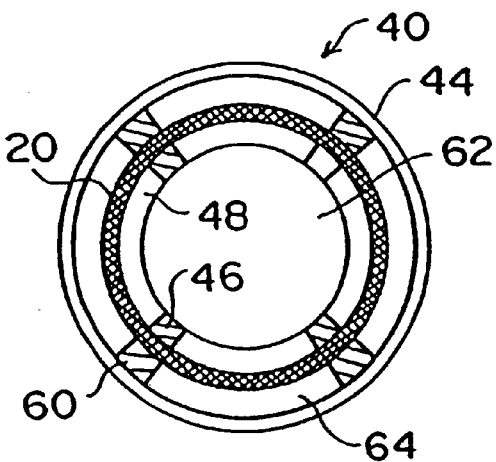
FIG. 11B is a cross-sectional view taken along lines XIB—XIB of FIG. 11A.

A sixth embodiment of the invention is depicted in FIGS. 10 and 11.

In this embodiment, the filter retainer 60 shown in FIG. 8 is formed into a cylindrical structure (that is, a caplike structure to cover a filter-mounting part 46 from its bottom side) having a bottom plate 70, and this bottom plate 70 is formed into a doughnut-shaped structure having a through hole in the middle. On the other hand, a protruding part 71 sticks out downward from a bottom plate 62 of the filter-mounting part 46, and the filter retainer 60 is fixed to the filter-mounting part 46 by forcing the filter-mounting part 46 upward until a protuberance 71a bulging radially outward from the protruding part 71 passes through the aforementioned through hole. Sealing elements 72, 59 are placed between the bottom plates 62 and 70 and between a lower end surface of a main body 44 of an upstream tube 40 and an upper end surface of the filter retainer 60, respectively, to prevent blood leakage from the upstream tube 40 into a downstream tube 42 with further increased reliability.

As shown in the foregoing embodiments, the filter-mounting part of the upstream tube is not specifically limited in its shape. As an example, the bottom of the upstream tube may be shaped to form a flat surface and a filter may be secured on thus structured bottom surface. As illustrated in the foregoing individual embodiments, however, if the filter-mounting part 16, 46 is designed to stick outward (inward as an alternative) from the upstream tube 10, 40 and the blood outlets 18, 48 are formed in the filter-mounting part 16, 46 forming a projecting part, it is possible to gain such advantage that a large total area (or blood flowing area) of the blood outlets is obtained.

Figure 12A:
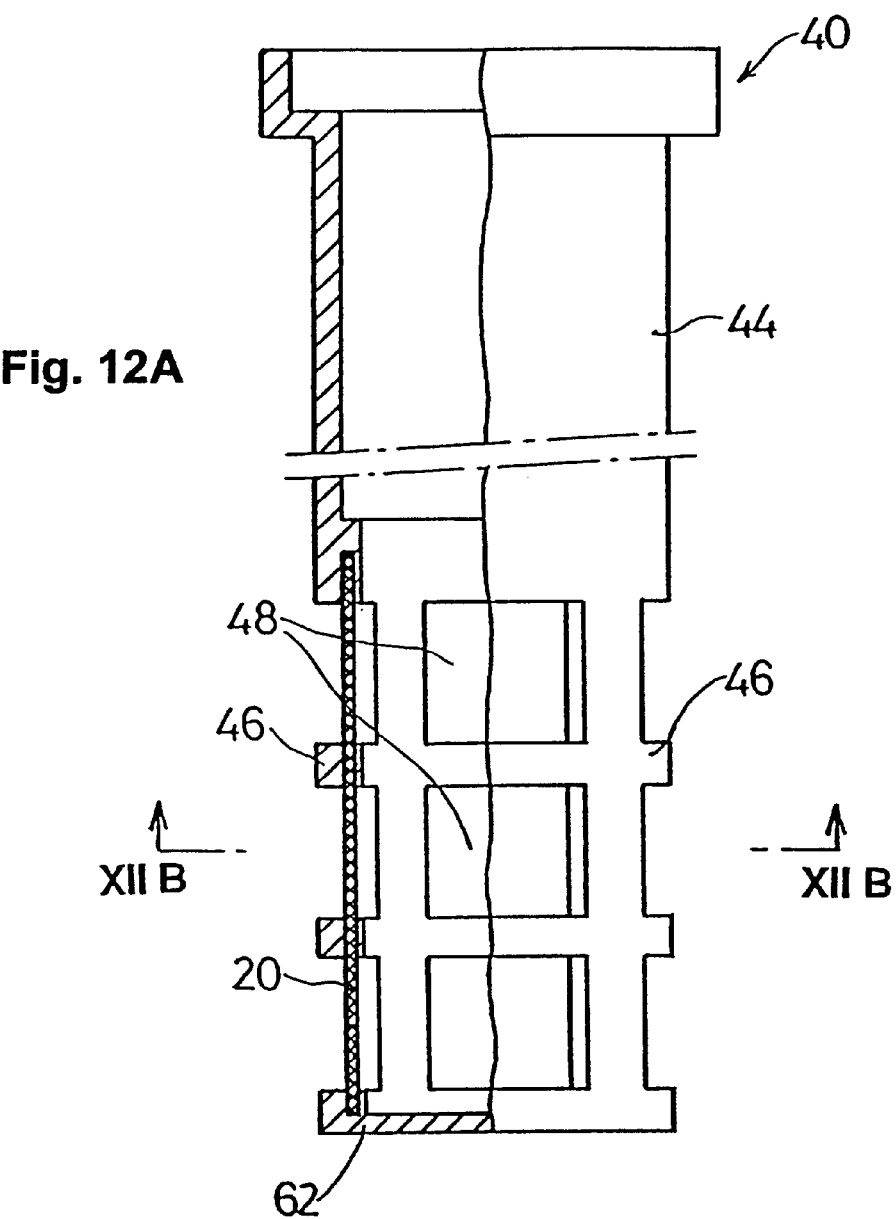
FIG. 12A is a partially sectional front view of an upstream tube according to a seventh embodiment of the invention.
Figure 12B:
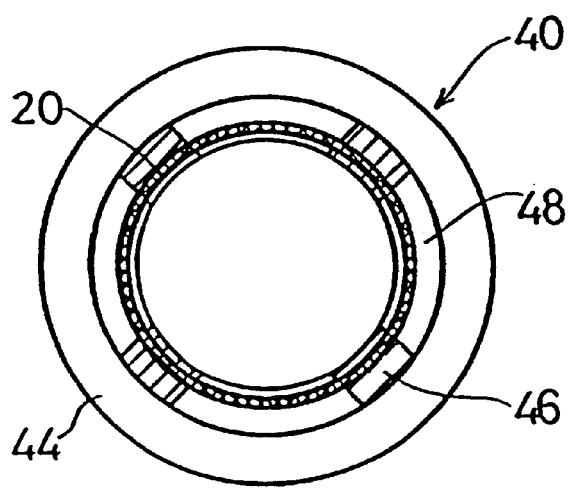
FIG. 12B is a cross-sectional view taken along lines XIIB—XIIB of FIG. 12A.

If, as a seventh embodiment, a filter-mounting part 46 and a filter 20 are one-piece molded as illustrated in FIGS. 12A and 12B, the aforementioned filter retainer becomes unnecessary and, then, it is possible to gain such advantage that the number of components can be reduced. This structure is applicable also to the upstream tube 11 to which the downstream tube 12 is directly connected as shown in FIG. 1, for example.

Figure 13:
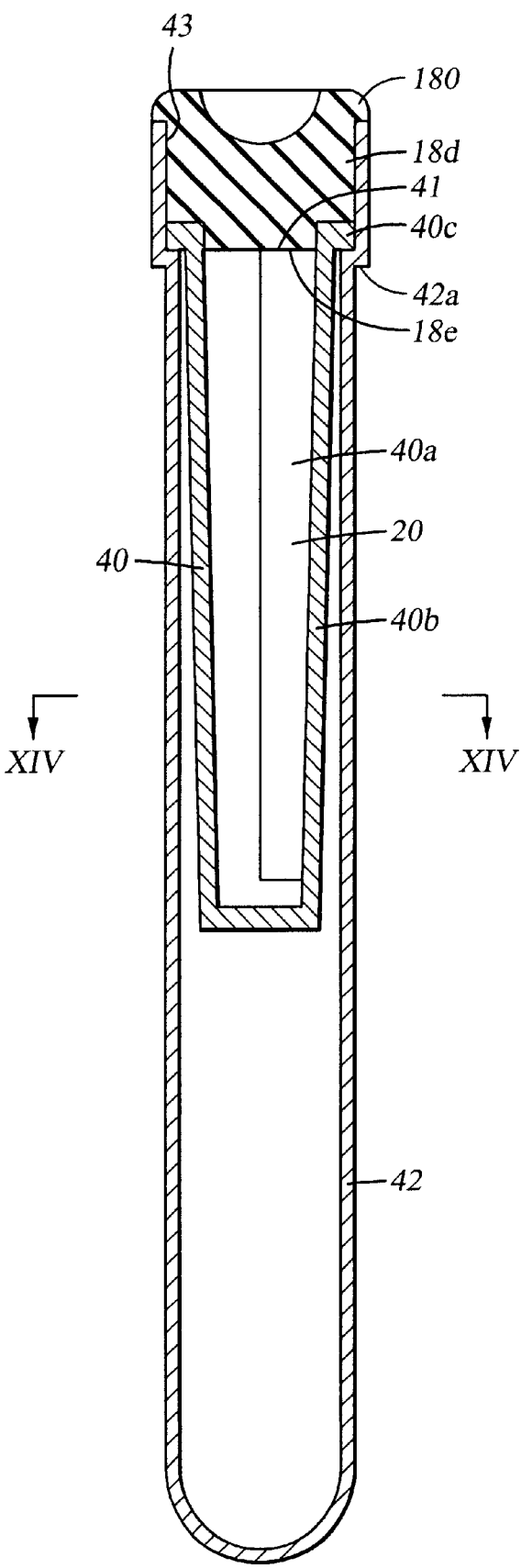
FIG. 13 is a cross-sectional front view of a blood-collecting tube according to an eighth embodiment of the invention.
Figure 14:
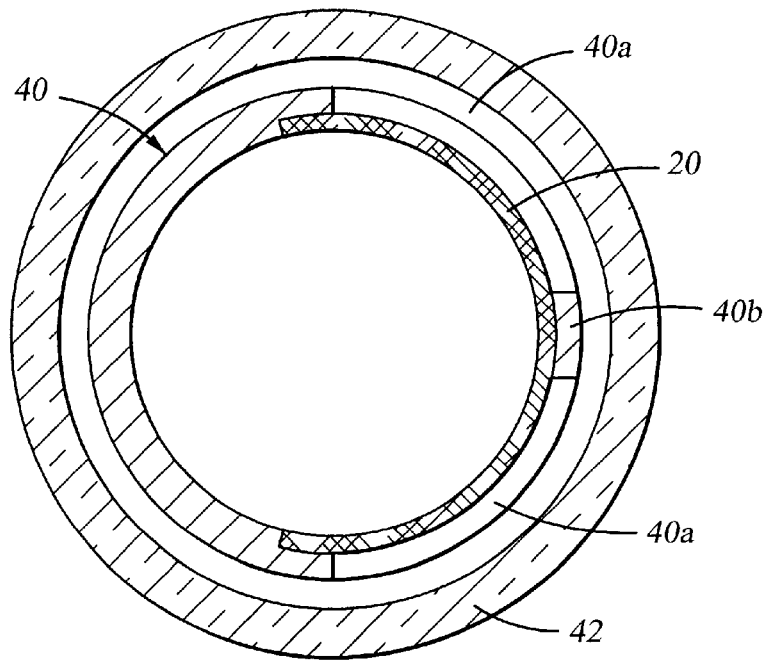
FIG. 14 is a cross-sectional view taken along lines XIV—XIV of FIG. 13.

An eighth embodiment of the invention is depicted in FIGS. 13 to 15.

This embodiment also employs an internal-external double-tube structure in which the whole of an upstream tube 40 is completely accommodated within a downstream tube 42, the whole upstream tube 40 being one-piece molded with a filter 20.

The upstream tube 40 has a blood inlet 41 forming an opening and the bottom of the upstream tube 40 is completely closed by a bottom plate. A side wall of the upstream tube 40 is formed into a tapered shape so that the diameter of the side wall gradually decreases toward the bottom (i.e., in a direction away from the opening at an upper end). This tapered shape is used in order that a metal mold can be smoothly removed downward in one-piece molding operation of the upstream tube 40.

A plurality of vertically extending windows (two in the illustrated example) are formed in the side wall so that each rib 40b, which also extends vertically, is flanked by the adjacent windows, the individual windows constituting blood outlets 40a. The filter 20 is formed integrally with the upstream tube 40 in such a way that the filter 20 blocks the blood outlets 40a from inside. More specifically, both circumferential ends of the filter 20, which is curled in arc-shaped form, are integrally embedded in a peripheral portion of each blood outlet 40a.

The earlier discussion of the first embodiment applies to the material for the above-described filter 20 as well.

The downstream tube 42, which is larger than the upstream tube 40, is of a shape having an opening 43 at an upper end only, and a peripheral portion of the opening 43, together with a peripheral portion of the blood inlet 41 of the upstream tube 40, is fitted into a common plug 180. Specifically, a large-diameter portion (first fitting part) 18d is formed on the plug 180 leaving its upper end portion, immediately below the upper end portion, while a small-diameter portion (second fitting part) 18e having a smaller diameter than the large-diameter portion 18d protrudes downward from a central part of the large-diameter portion 18d so that the small-diameter portion 18e can be fitted into the blood inlet 41 of the aforementioned upstream tube 40 without creating any gap and the large-diameter portion 18d can be fitted into the upper-end opening 43 of the aforementioned downstream tube 42 without creating any gap.

Furthermore, as a characteristic feature of this construction, there is formed a flange 40c (protruding part) extending radially outward from a peripheral portion of the blood inlet of the aforementioned downstream tube 42 while an elevated step 42a, which is shaped such that its lower side is raised inward from its upper side, is formed at an appropriate upper part of the downstream tube 42. This construction permits the upstream tube 40 to be inserted into the downstream tube 42 up to a point where the aforementioned flange 40c comes into contact with the elevated step 42a.

Figures 15A, 15B:
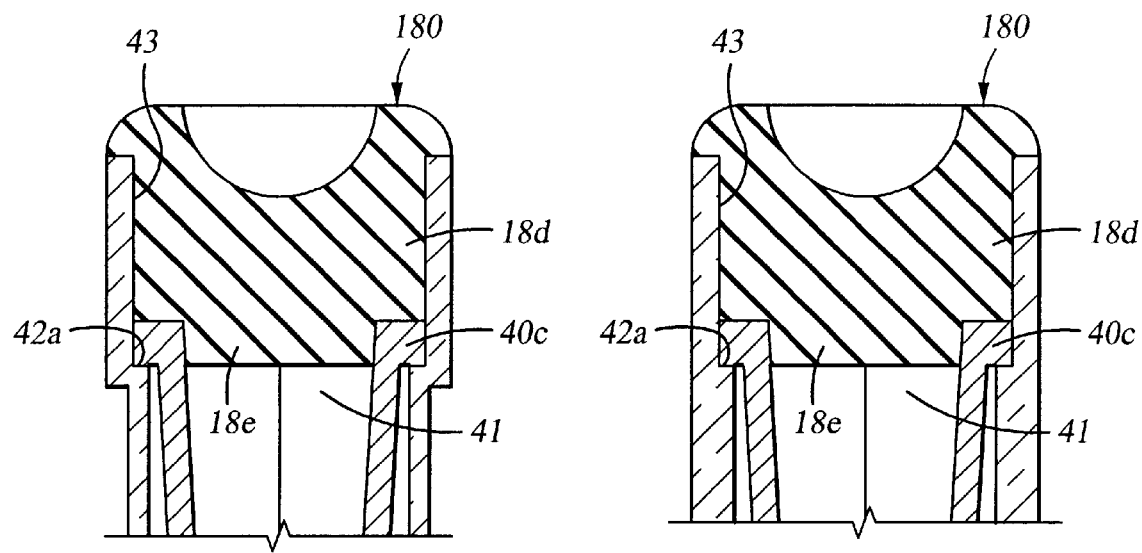
FIG. 15A is a cross-sectional front view showing a principal portion of the blood-collecting tube depicted in FIG. 13.
FIG. 15B is a cross-sectional front view showing a variation of the principal portion.

The construction of this elevated step 42a may either be such that the step is formed maintaining a fixed wall thickness of the downstream tube 42 as shown in FIG. 15A or the inside of an upper portion of the downstream tube 42 is cut out reducing its thickness and thereby forming a stepped stage connecting toward a lower portion as shown in FIG. 15B. Furthermore, instead of the flange 40c which bulges radially outward all around, there may be formed protruding parts which are provided on the upstream tube 40 along its circumference at particular intervals.

According to this construction, it is possible to simultaneously fit the small-diameter portion 18e and the large-diameter portion 18d into the blood inlet 41 and the opening 43, respectively. This is achieved by fitting the plug 18 from above the flange 40c with the flange 40c readily hooked on the elevated step 42a. This means that the plug 180 can be simultaneously fitted into both of the tubes 40, 42 in a single operation. It is therefore possible to significantly improve assembly operation compared to, for example, the aforementioned arrangement of FIG. 6 in which the upper ends of the tubes 40, 42 are fitted into the respective grooves 18b,

18c. Furthermore, since the flange 40c is sandwiched between the plug 180 and the elevated step 42a when they are assembled, it is possible to secure the upstream tube 40 within the downstream tube 42 in a more stable manner.

Upon completion of assembly, it is possible to quickly collect blood by a procedure similar to that of the foregoing embodiments.

Specifically, the plug 180 is pierced with a suction tube so that its one end is positioned within the internal space of the upstream tube 10, and air within the two tubes 40, 42 is drawn to thereby depressurize the interior of the tubes 40, 42 up to an appropriate degree of vacuum complying with the specifications by a manufacturer or a user. Then, one end (upper end as illustrated) of a blood-drawing needle N as shown by alternate long and two short dashed lines in FIG. 1 is stuck and the other end (lower end in FIG. 1) is passed through the plug 180 so that the plug 180 is pierced by the blood-drawing needle N. As a consequence, blood in a blood vessel automatically flows into the upstream tube 40 due to a negative pressure within the upstream tube 40. Then, due to a pressure difference between the two tubes 40, 42 corresponding to the amount of the blood drawn in, the blood gains a tendency to flow into the downstream tube 42 through the blood outlets 40a. At this stage, cellular components contained in the blood is prohibited from passing through the filter 20 whereas only its plasma components are allowed to pass through the filter 20 into the downstream tube 42. It is therefore possible to carry out blood separation while performing blood collection.

After the plasma components have been collected into the downstream tube 42 in this manner, the upstream tube 40 may be separated from the downstream tube 42 together with the plug 180, or the upstream tube 40 may be separated from the downstream tube 42 after removing the plug 180 from the two tubes 40, 42. Then, the downstream tube 42 can be used as it is as a test tube in subsequent examination.

While the present invention has been described above with respect to a few preferred embodiments thereof, it should of course be understood that it should not be limited thereto but various changes or modifications may be made in any acceptable manner without departing from the spirit and scope of the invention as defined in the appended claims.

We claim:

1. A blood-collecting tube comprising:
   an upstream tube having a blood inlet and a blood outlet;
   a plug fitted to the blood inlet for closing the upstream tube, the plug adapted for being pieced by a blood-drawing needle;
   a filter for covering the whole area of the blood outlet and for separating blood into cellular and plasma components; and
   a downstream tube directly and detachably connected to the upstream tube, wherein threaded portions mating each other are formed on the upstream tube and the downstream tube respectively; and wherein the blood-collecting tube has a negative pressure before blood collection begins.

2. A blood-collecting tube comprising:
   an upstream tube having a blood inlet and a blood outlet;
   a plug fitted to the blood inlet for closing the upstream tube, the plug adapted for being pieced by a blood-drawing needle;
   a filter for covering the whole area of the blood outlet and for separating blood into cellular and plasma components; and a downstream tube detachably connected to the upstream tube, wherein the downstream tube is shaped such that it has an opening at one end and accommodates the whole upstream tube, and the opening of the downstream tube is fitted together with the blood inlet of the upstream tube to the plug; and wherein the blood-collecting tube has a negative pressure before blood collection begins.

3. A blood-collecting tube as defined in claim 2, wherein the plug has a first fitting part which can be fitted into the opening of the downstream tube and a second fitting part which protrudes from the first fitting part and can be fitted into the blood inlet of the upstream tube.

4. A blood-collecting tube as defined in claim 3, wherein the upstream tube has a protruding part extending radially outward at a peripheral portion of the blood inlet thereof, and the downstream tube has an elevated step extending inward on an inner surface and close to its open end thereof so that the upstream tube can be inserted into the downstream tube up to a point where the protruding part hooks onto the elevated step.

5. A blood-collecting tube comprising:

an upstream tube having a blood inlet and a blood outlet, wherein part of the upstream tube is formed with a projecting part projecting inward or outward and the blood outlet is provided in the projecting part;

a plug fitted to the blood inlet for closing the upstream tube, the plug adapted for being pierced by a blood-drawing needle;

a filter for covering the whole area of the blood outlet and for separating blood into cellular and plasma components; and a downstream tube for enclosing the filter and the blood outlet and the interior of the downstream tube is sealed, and the downstream tube is attachable to and detachable from the upstream tube.

6. A blood-collecting tube comprising:

an upstream tube having a blood inlet and a blood outlet, wherein part of the upstream tube is formed with a projecting part projecting inward or outward and the blood outlet is provided in the projecting part, the projecting part being shaped in a generally triangular form, a plug fitted to the blood inlet for closing the upstream tube, the plug adapted for being pieced by a blood-drawing needle;

a filter for covering the whole area of the blood outlet and for separating blood into cellular and plasma components, wherein the filter is shaped in a generally rectangular form and is disposed to cover the blood outlet; and a downstream tube detachably connected to the upstream tube; and wherein the blood-collecting tube has a negative pressure before blood collection begins.

7. A blood-collecting tube comprising:

an upstream tube having a blood inlet and a blood outlet, wherein part of the upstream tube is formed with a projecting part projecting inward or outward and the blood outlet is provided in the projecting part, wherein the projecting part is so shaped in a cylindrical form, the blood outlet is provided at least in a surrounding wall of the projecting part, and the filter shaped in a cylindrical form is disposed to cover the blood outlet;

a plug fitted to the blood inlet for closing the upstream tube, the plug adapted for being pierced by a blood-drawing needle;

a filter for covering the whole area of the blood outlet and for separating blood into cellular and plasma components; and a downstream tube for enclosing the filter and the blood outlet and the interior of the downstream tube is sealed, and the downstream tube is attachable to and detachable from the upstream tube.

8. A blood-collecting tube as recited in claim 1, further comprising a filter retainer for pressingly securing the filter to the blood outlet of the upstream tube from the outside.

9. A blood-collecting tube comprising:

an upstream tube having a blood inlet and a blood outlet, wherein the upstream tube and the filter are molded into a single structure, and the upstream tube is formed into a taper, having a diameter decreasing in a direction away from the blood inlet;

a plug fitted to the blood inlet for closing the upstream tube, the plug adapted for being pierced by a blood-drawing needle;

a filter for covering the whole area of the blood outlet and for separating blood into cellular and plasma components;

a downstream tube for enclosing the filter and the blood outlet and the interior of the downstream tube is sealed, and the downstream tube is attachable to and detachable from the upstream tube.

* * * * *

UNITED STATES PATENT AND TRADEMARK OFFICE
CERTIFICATE OF CORRECTION

PATENT NO. : 6,506,167 B1
DATED : January 14, 2003
INVENTOR(S) : Ishimoto et al.

It is certified that error appears in the above-identified patent and that said Letters Patent is hereby corrected as shown below:

<u>Title page,</u>
Item [12], United States Patent, replace "Ishimito et al." with -- Ishimoto et al. --.
Item [75], Inventors, replace "Tetsushi Ishimito" with -- Tetsushi Ishimoto --.

Signed and Sealed this

Seventeenth Day of June, 2003

JAMES E. ROGAN
*Director of the United States Patent and Trademark Office*